United States Patent
Muraya

(10) Patent No.: US 11,649,274 B2
(45) Date of Patent: May 16, 2023

(54) METHOD FOR PRODUCING MESENCHYMAL STEM CELL AND APPLICATION OF SAME

(71) Applicant: FUJIFILM Corporation, Tokyo (JP)

(72) Inventor: Koji Muraya, Ashigarakami-gun (JP)

(73) Assignee: FUJTFITM Corporation, Tokyo (JP)

(*) Notice: Subject to any disclaimer, the term of this patent is extended or adjusted under 35 U.S.C. 154(b) by 567 days.

(21) Appl. No.: 16/678,873

(22) Filed: Nov. 8, 2019

(65) Prior Publication Data
US 2020/0140523 A1 May 7, 2020

Related U.S. Application Data

(63) Continuation of application No. PCT/JP2018/018391, filed on May 11, 2018.

(30) Foreign Application Priority Data

May 12, 2017 (JP) .............................. JP2017-095463

(51) Int. Cl.
*C12N 5/0775* (2010.01)
*C07K 14/78* (2006.01)

(52) U.S. Cl.
CPC ............ *C07K 14/78* (2013.01); *C12N 5/0663* (2013.01); *C12N 2501/40* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 6,992,172 B1* | 1/2006 | Chang ...................... | A61K 8/65 435/320.1 |
| 2010/0209382 A1 | 8/2010 | Alexander-Bridges et al. | |
| 2010/0227399 A1 | 9/2010 | Funaki et al. | |
| 2012/0329157 A1* | 12/2012 | Nakamura ............ | C12N 5/0068 435/395 |
| 2013/0004549 A1 | 1/2013 | Nakamura et al. | |
| 2015/0004146 A1* | 1/2015 | Peled ................... | C12N 5/0667 424/93.7 |
| 2016/0074471 A1 | 3/2016 | Ko et al. | |
| 2018/0064849 A1 | 3/2018 | Nakamura et al. | |

FOREIGN PATENT DOCUMENTS

| CN | 102791301 A | 11/2012 |
|---|---|---|
| JP | 3-228683 A | 10/1991 |
| JP | 2007-326834 A | 12/2007 |
| JP | 2013-234150 A | 11/2013 |
| JP | 2014-198686 A | 10/2014 |
| JP | 2015-43780 A | 3/2015 |
| WO | WO 2008/103041 A1 | 8/2008 |
| WO | WO 2011/006087 A1 | 1/2011 |
| WO | WO 2011/108537 A1 | 9/2011 |
| WO | WO 2014/178653 A1 | 11/2014 |
| WO | WO 2016/148245 A1 | 9/2016 |

OTHER PUBLICATIONS

DeLuca et al., Oxidative Medicine and Cellular Longevity, vol. 2016, Article ID 4389410, 14 pages (Year: 2016).*
Gallow et al., J. Funct. Biomater. 2020, 11, 79 (Year: 2020).*
Yamada et al., BioMed Research International, vol. 2014, Article ID 302932, 8 pages (Year: 2014).*
Extended European Search Report, dated Jul. 13, 2020, for corresponding European Application No. 18798627.8.
International Preliminary Report on Patentability and English translation of the Written Opinion of the International Searching Authority (Forms PCT/IB/326, PCT/IB/373, and PCT/ISA/237) for International Application No. PCT/JP2018/018391, dated Nov. 21, 2019.
International Search Report (Form PCT/ISA/210) for International Application No. PCT/JP2018/018391, dated Aug. 14, 2018, with English translation.
Lin et al., "Inhibition of Adipogenesis by RGD-dependent disintegrin", Biochem. Pharmacol., vol. 70, No. 10, Nov. 15, 2005, pp. 1469-1478.
Liu et al., "Potential Application of Hydrolyzed Fish Collagen for Inducing the Multidirectional Differentiation of Rat Bone Marrow Mesenchymal Stem Cells", Biomacromolecules, vol. 15, No. 1, Jan. 13, 2014, pp. 436-443.

(Continued)

*Primary Examiner* — Evelyn Y Pyla
(74) *Attorney, Agent, or Firm* — Birch, Stewart, Kolasch & Birch, LLP

(57) ABSTRACT

An object of the invention is to provide a method for producing a mesenchymal stem cell in which differentiation into an adipocyte is suppressed with a simple step, a mesenchymal stem cell, a method for producing a differentiation-induced cell using the method for producing a mesenchymal stem cell described above, a differentiation-induced cell, and an inhibitor of differentiation into an adipocyte. According to the invention, there is provided a method for producing a mesenchymal stem cell, including: a step of culturing a mesenchymal stem cell in a liquid medium in which a recombinant gelatin having an amino acid sequence derived from a partial amino acid sequence of collagen has been dissolved, wherein differentiation into an adipocyte is suppressed.

10 Claims, 7 Drawing Sheets

Specification includes a Sequence Listing.

(56) References Cited

OTHER PUBLICATIONS

Japanese Office Action for corresponding Japanese Application No. 2019-517724, dated Dec. 8, 2020, with an English translation.
Japanese Decision of Refusal for corresponding Japanese Application No. 2019-517724, dated Jun. 1, 2021, with an English translation.
Chinese Office Action and Search Report for corresponding Chinese Application No. 201880031304.0, dated Oct. 20, 2022, with an English translation.
Morandi et al., "ITGAV and ITGA5 diversely regulate proliferation and adipogenic differentiation of human adipose derived stem cells," Scientific Reports, vol. 6, No. 28889, 2016, 14 pages total.
Peng, "Effects of cell shape, spreading size and cell density on differentiation of stem cells on micropatterned surfaces of a polymeric hydrogel," [Dissertation], Fudan University, 2012, 211 pages total, with an English abstract.

* cited by examiner

METHOD FOR PRODUCING MESENCHYMAL STEM CELL AND APPLICATION OF SAME

CROSS-REFERENCE TO RELATED APPLICATIONS

This application is a Continuation of PCT International Application No. PCT/JP2018/018391 filed on May 11, 2018, which claims priority under 35 U.S.C § 119(a) to Japanese Patent Application No. 2017-095463 filed on May 12, 2017. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2870-0732PUS1_ST25.txt" created on Jan. 6, 2020 and is 12,000 bytes in size. The sequence listing contained in this .txt file is part of the specification and is hereby incorporated by reference herein in its entirety.

BACKGROUND OF THE INVENTION

1. Field of the Invention

The present invention relates to a method for producing a mesenchymal stem cell in which differentiation into an adipocyte is suppressed with a simple step. The invention relates to a method for producing a differentiation-induced cell, including a step of culturing the mesenchymal stem cell in which differentiation into an adipocyte is suppressed in a medium for inducing differentiation. The invention relates to a mesenchymal stem cell and a differentiation-induced cell produced by the method. The invention further relates to an inhibitor of differentiation into an adipocyte.

2. Description of Related Art

A basis of development of obesity and metabolic syndrome associated with adipocyte accumulation in vivo is an inflammatory response by macrophages present in accumulated adipocytes. An origin of the adipocytes is mesenchymal stem cells, from which bone cells, chondrocytes, cardiomyocytes, and adipocytes are induced. A method for suppressing differentiation of the mesenchymal stem cells is studied.

JP2015-043780A describes a method for storing a mesenchymal stem cell population using a gel and a matrix having stiffness in a range of 150 to 750 kPa. JP2014-198686A describes an adipose differentiation inhibitor containing, as an active ingredient, a cyclic peptide having a sequence similar to one of cysteine-rich domains of RANK (NF-κB receptor activator). JP1991-228683A (JP-H3-228683A) describes a peptide having a specified amino acid sequence and having an activity of inducing suppression of proliferation and differentiation of human bone marrow stem cells. JP2007-326834A describes a polypeptide which is obtained by expressing a polypeptide obtained from a sequence of human Deltal in a prokaryotic cell with the smallest unit and purifying the polypeptide by using a denaturant and a reducing agent and has stem cell differentiation-inhibiting activity.

On the other hand, gelatin is known as a typical scaffold material in a regenerative medicine. Gelatin has a high biocompatibility and is known as a highly safe material. Gelatin has a high track record of application in medical applications. WO2011/108537A describes a cell support formed from a gelatin formed by recombinant (recombinant gelatin) and formed from a porous body having predetermined characteristics.

SUMMARY OF THE INVENTION

In JP2015-043780A, a gel having a predetermined stiffness is produced by mixing acrylamide and bisacrylamide in a ratio within a predetermined range and gelling, but an operation is complicated. JP2014-198686A, JP1991-228683A (JP-H3-228683A), and JP2007-326834A describe that differentiation into adipocytes is suppressed by using a peptide or a polypeptide, but a method for suppressing the differentiation of mesenchymal stem cells into adipocytes with a simpler step is desired.

An object of the invention is to provide a method for producing a mesenchymal stem cell in which differentiation into an adipocyte is suppressed with a simple step and a mesenchymal stem cell produced by the method. Another object of the invention is to provide a method for producing a differentiation-induced cell using the method for producing a mesenchymal stem cell described above, and a differentiation-induced cell produced by the method. Still another object of the invention is to provide an inhibitor of differentiation into an adipocyte.

The present inventors have intensively studied to achieve the above objects. As a result, it was found that, by culturing a mesenchymal stem cell in a liquid medium in which a recombinant gelatin having an amino acid sequence derived from a partial amino acid sequence of collagen has been dissolved, it is possible to produce a mesenchymal stem cell in which differentiation into an adipocyte is suppressed. The invention has been completed based on these findings.

That is, according to the invention, the following inventions are provided.

<1> A method for producing a mesenchymal stem cell, including:
a step of culturing a mesenchymal stem cell in a liquid medium in which a recombinant gelatin having an amino acid sequence derived from a partial amino acid sequence of collagen has been dissolved,
in which differentiation into an adipocyte is suppressed.

<2> The method according to <1>,
in which the recombinant gelatin has repeats of a sequence represented by Gly-X-Y, which is characteristic to collagen,
X and Y each independently represent any one amino acid residue,
a plurality of the Gly-X-Y sequences may be identical to or different from one another, and
a molecular weight of the recombinant gelatin is from 2 kDa to 100 kDa.

<3> The method according to <1> or <2>,
in which the recombinant gelatin has repeats of a sequence represented by Gly-X-Y, which is characteristic to collagen,
X and Y each independently represent any one amino acid residue,
a plurality of the Gly-X-Y sequences may be identical to or different from one another, and
a molecular weight of the recombinant gelatin is from 10 kDa to 90 kDa.

<4> The method according to any one of <1> to <3>,
in which the recombinant gelatin has repeats of a sequence represented by Gly-X-Y, which is characteristic to collagen, X and Y each independently represent any one amino acid residue, a plurality of the Gly-X-Y sequences may be identical to or different from one another, and the recombinant gelatin includes two or more sequences of cell adhesion signals in one molecule.

<5> The method according to <4>,
in which the cell adhesion signal is an amino acid sequence represented by Arg-Gly-Asp.

<6> The method according to any one of <1> to <5>,
in which the amino acid sequence of the recombinant gelatin is represented by the following formula, A-[(Gly-X-Y)$_n$]$_m$-B, in the formula, A represents any amino acid residue or amino acid sequence; B represents any amino acid residue or amino acid sequence; n units of X each independently represent any one amino acid residue; n units of Y each independently represent any one amino acid residue; n represents an integer from 3 to 100; m represents an integer from 2 to 10; and n units of Gly-X-Y may be identical to or different from one another.

<7> The method according to any one of <1> to <6>,
in which the amino acid sequence of the recombinant gelatin is represented by the following formula, (SEQ ID NO: 11)
Gly-Ala-Pro-[(Gly-X-Y)$_{63}$]$_3$-Gly, in the formula, 63 units of X each independently represent any one amino acid residue; 63 units of Y each independently represent any one amino acid residue; and 63 units of Gly-X-Y may be identical to or different from one another.

<8> The method according to any one of <1> to <7>,
in which the recombinant gelatin includes (1) an amino acid sequence set forth in SEQ ID NO:1; or (2) an amino acid sequence having cell adhesiveness and having at least 80% sequence identity with the amino acid sequence set forth in SEQ ID NO:1.

<9> The method according to any one of <1> to <8>,
in which the mesenchymal stem cell is a bone marrow-derived cell or a cartilage-derived cell.

<10> The method according to any one of <1> to <9>,
in which the liquid medium in which a recombinant gelatin having an amino acid sequence derived from a partial amino acid sequence of collagen has been dissolved is a liquid medium for maintaining undifferentiation.

<11> The method according to any one of <1> to <10>,
in which a concentration of the recombinant gelatin having an amino acid sequence derived from a partial amino acid sequence of collagen in the liquid medium in which the recombinant gelatin has been dissolved is from 0.01 μg/mL to 500 μg/mL.

<12> The method according to any one of <1> to <10>,
in which a concentration of the recombinant gelatin having an amino acid sequence derived from a partial amino acid sequence of collagen in the liquid medium in which the recombinant gelatin has been dissolved is from 0.02 μg/mL to 300 μg/mL.

<13> A method for producing a differentiation-induced cell, including:

a step of producing a mesenchymal stem cell in which differentiation into an adipocyte is suppressed by the method according to any one of <1> to <12>; and a step of culturing the mesenchymal stem cell in which differentiation into an adipocyte is suppressed in a medium for inducing differentiation.

<14> A mesenchymal stem cell produced by the method according to any one of <1> to <12>.

<15> A differentiation-induced cell produced by the method according to <13>.

<16> An inhibitor of differentiation into an adipocyte, including:

a recombinant gelatin having an amino acid sequence derived from a partial amino acid sequence of collagen.

According to the method for producing a mesenchymal stem cell according to an aspect of the invention, it is possible to produce a mesenchymal stem cell in which differentiation into an adipocyte is suppressed with a simple step. According to the method for producing a differentiation-induced cell using the method for producing a mesenchymal stem cell described above, it is possible to produce a desired cell with a simple step. The mesenchymal stem cell and the differentiation-induced cell produced by the method of aspects of the invention are useful in regenerative medicine or the like. According to the inhibitor of differentiation into an adipocyte according to an aspect of the invention, it is possible to produce a mesenchymal stem cell in which differentiation into an adipocyte is suppressed with a simple step.

BRIEF DESCRIPTION OF THE DRAWINGS

FIG. 6A shows a case of fat differentiation using an adipogenic differentiation induction medium of Lonza, and FIG. 6B shows a case of fat differentiation using an adipogenic differentiation induction medium of PromoCell.

DESCRIPTION OF THE PREFERRED EMBODIMENTS

Figure 1:
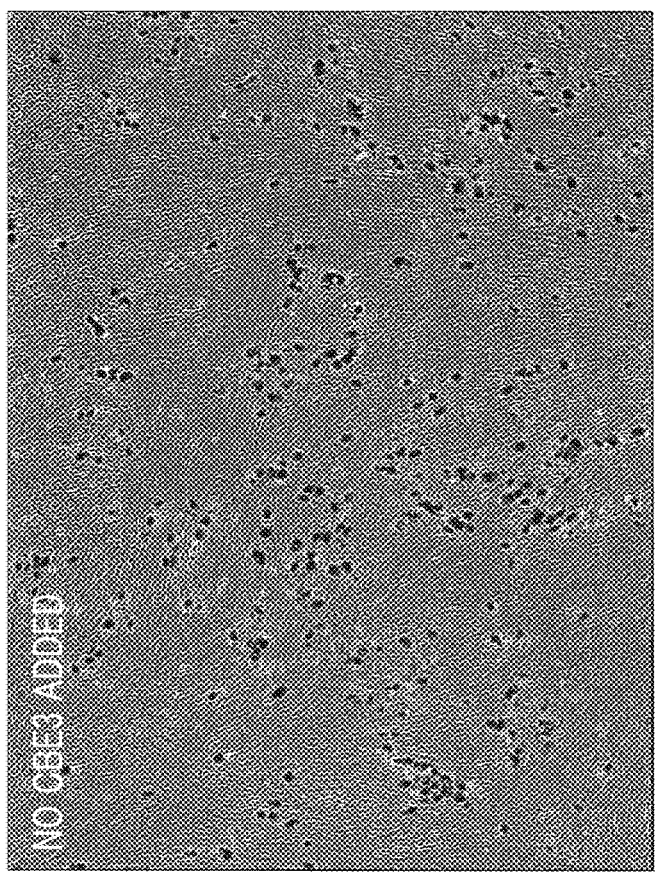
FIG. 1 shows results of confirming differentiation into adipocytes by staining cells with oil red, in a case in which the cells are UDE BM and a medium is MesenPro.
Figure 1:
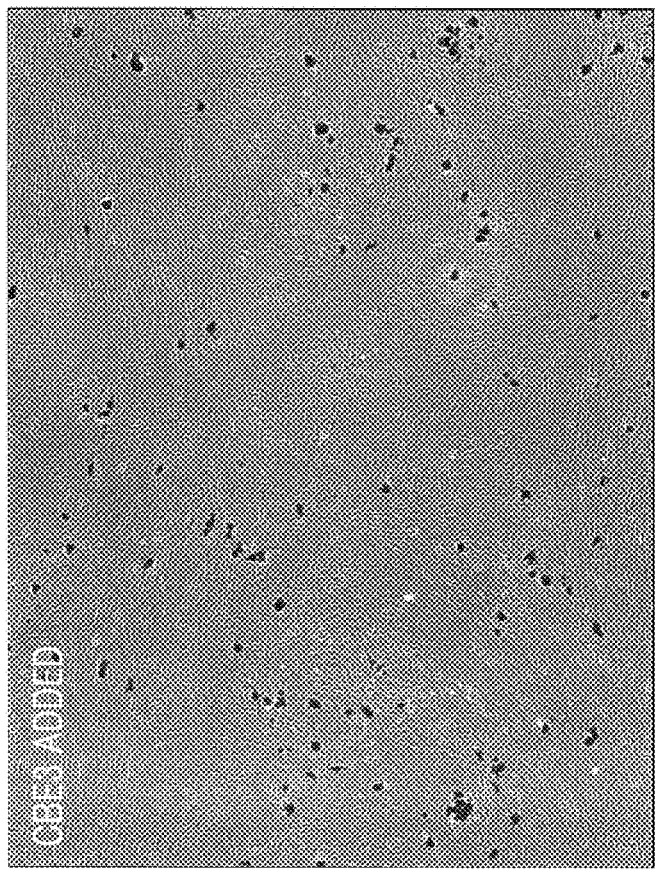
Figure 2:
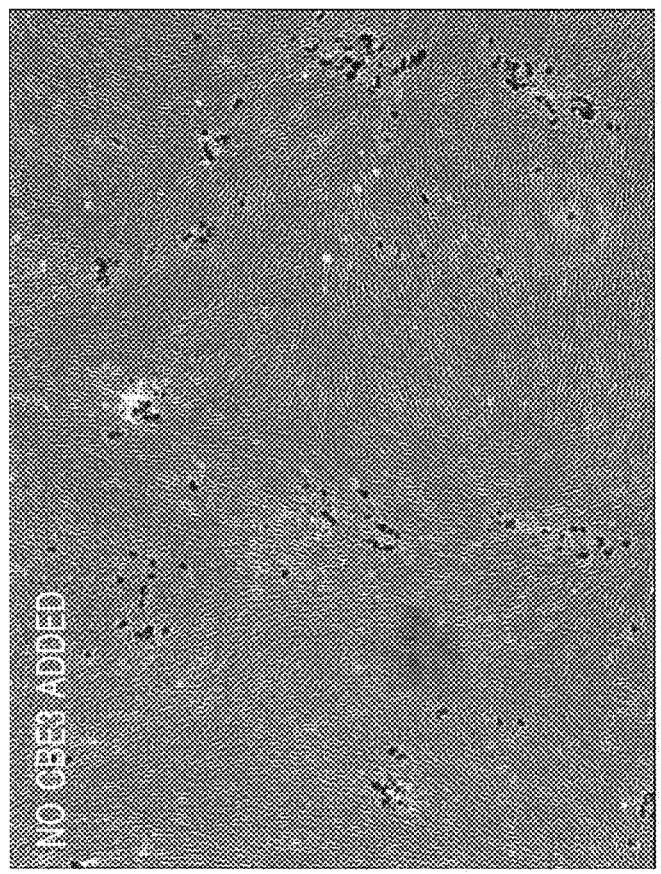
FIG. 2 shows results of confirming differentiation into adipocytes by staining cells with oil red, in a case in which the cells are UDE BM and a medium is DMEM.
Figure 2:
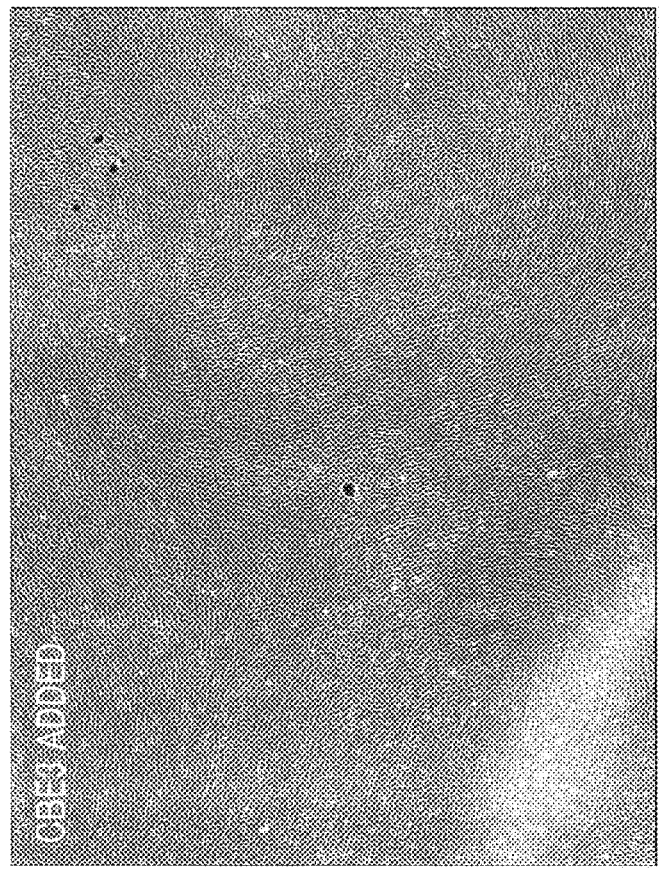
Figure 3:
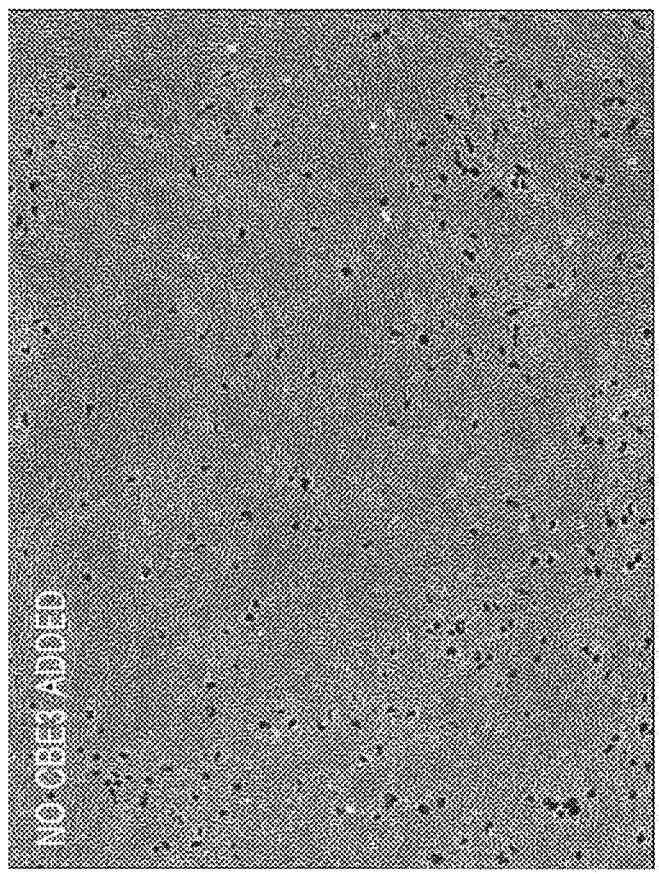
FIG. 3 shows results of confirming differentiation into adipocytes by staining cells with oil red, in a case in which the cells are UDE BM and a medium is PRIME-XV.
Figure 3:
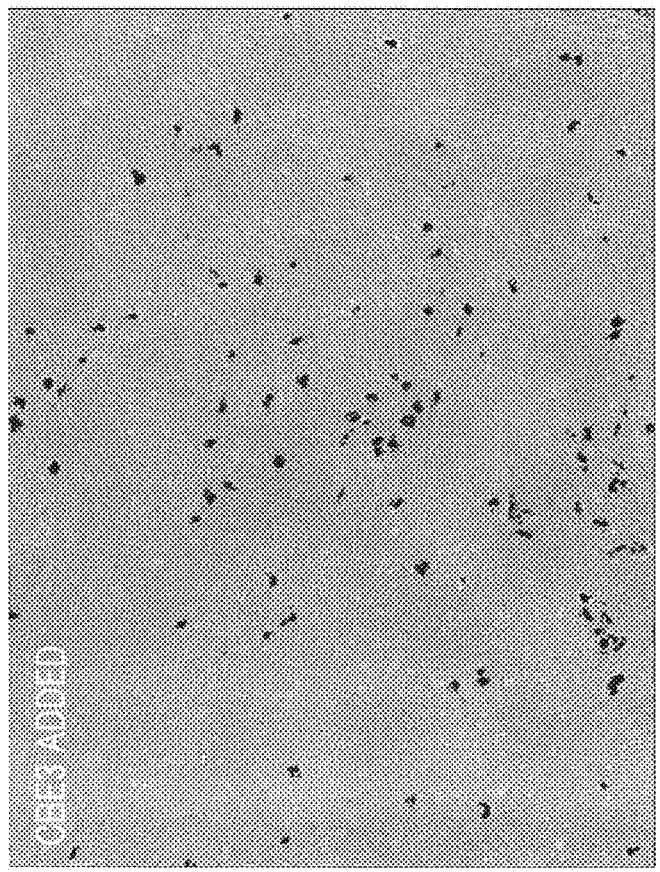
Figure 4:
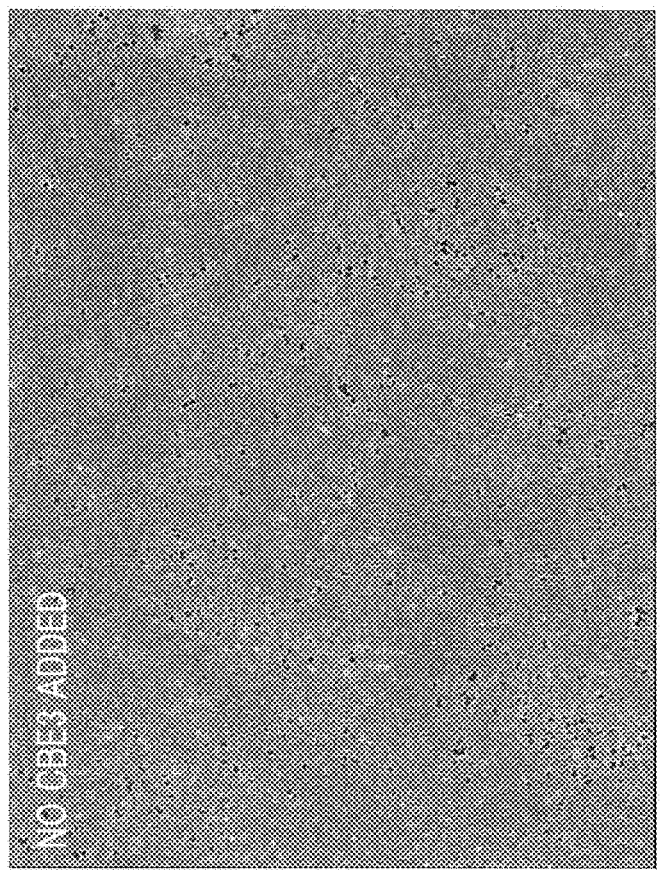
FIG. 4 shows results of confirming differentiation into adipocytes by staining the cells with oil red, in a case in which the cells are Yub2505 and a medium is PRIME-XV.
Figure 4:
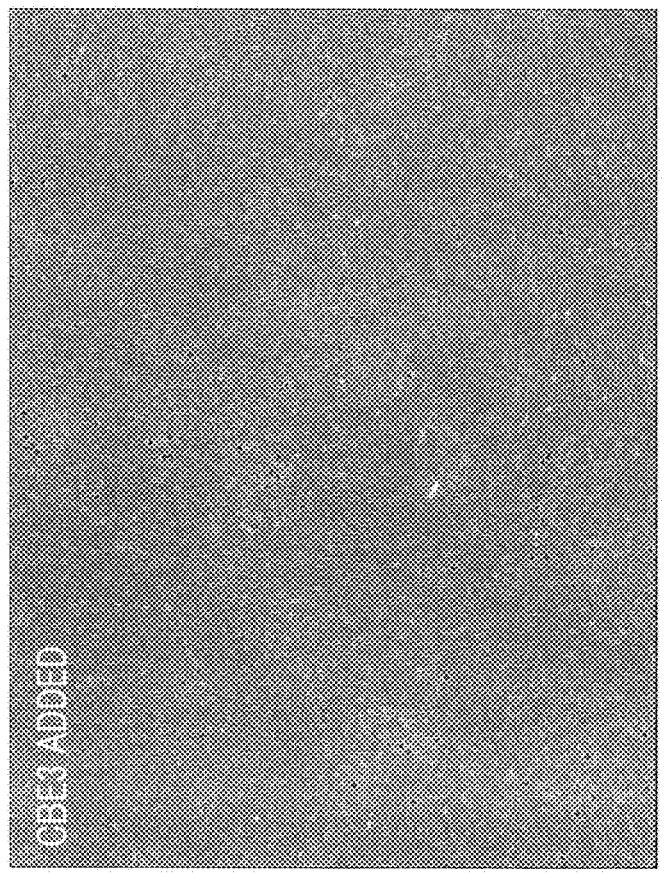
Figure 5A:
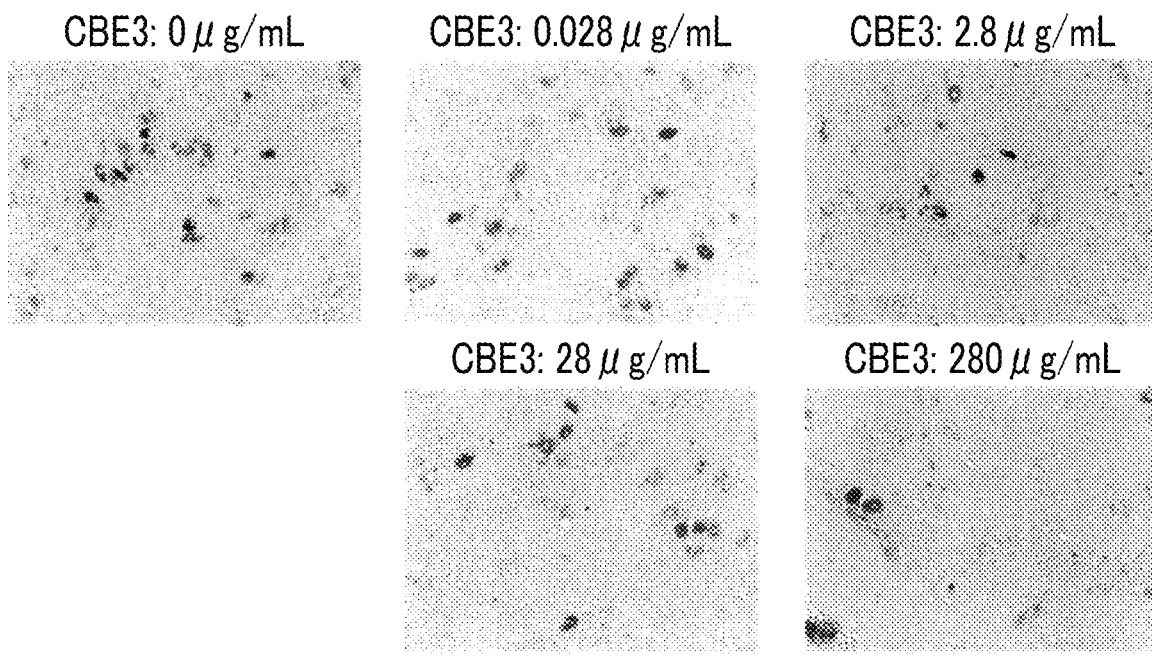
FIGS. 5A and 5B show results of confirming differentiation into adipocytes by staining cells, which are cultured with varying an addition amount of a recombinant gelatin in a case in which the cells are BMSC (Lonza: PT-2501) and a medium is MesenPro and then fat-differentiated using an adipogenic differentiation induction medium of Lonza (FIG. 5A) or PromoCell (FIG. 5B), with Nile red.
Figure 5B:
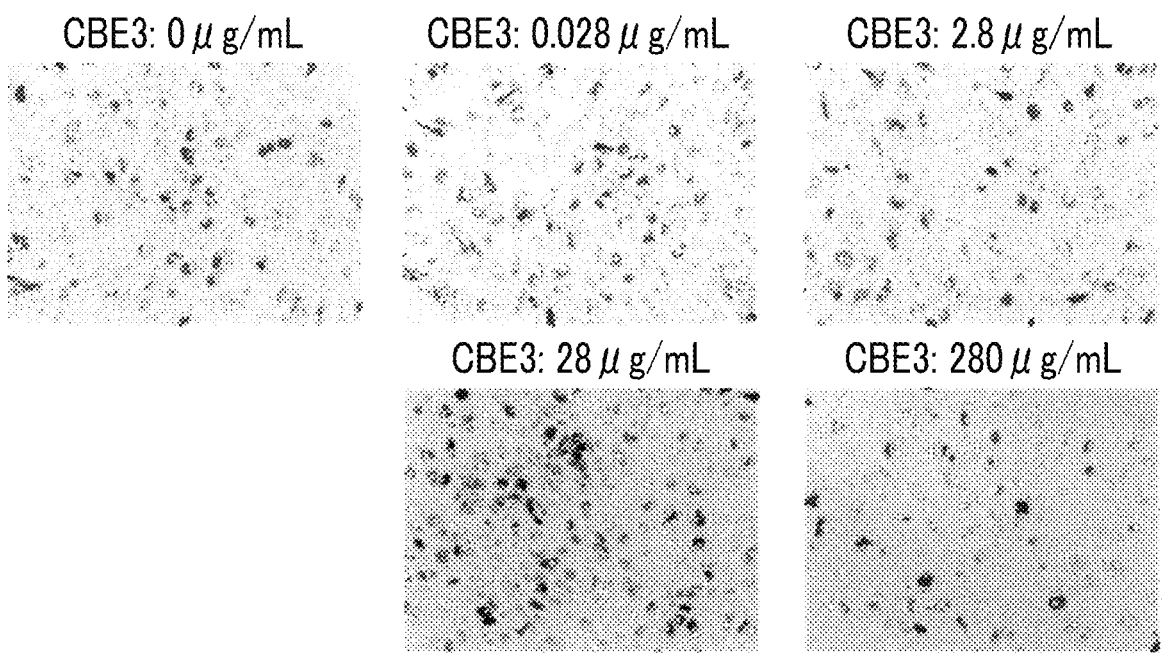

Hereinafter, embodiments of the invention will be described in detail.

The invention relates to a method for producing a mesenchymal stem cell in which differentiation into an adipocyte is suppressed. In particular, the method includes a step of culturing a mesenchymal stem cell in a liquid medium in which a recombinant gelatin having an amino acid sequence derived from a partial amino acid sequence of collagen has been dissolved.

According to the invention, differentiation of mesenchymal stem cells into adipocytes can be suppressed.

In a case of performing cell therapy using mesenchymal stem cells, it is important to avoid tissue differentiation of mesenchymal stem cells that are susceptible to surrounding microenvironment in vivo in unintended directions (for example, into adipocytes) in terms of ensuring therapeutic effects. The cells obtained by the method of an embodiment of the invention can be used for, for example, bone tissue repair or cartilage tissue repair in regenerative medicine.

In the invention, a mesenchymal stem cell is cultured in a liquid medium in which a recombinant gelatin having an amino acid sequence derived from a partial amino acid sequence of collagen has been dissolved. Timing during which mesenchymal stem cells are cultured in the liquid medium in which a recombinant gelatin has been dissolved, is not particularly limited, and may be any of the time of maintenance or expansion culture of the mesenchymal stem cells or the time of differentiation induction culture of mesenchymal stem cells and may also be both of them.

Preferably, at the time of maintenance or expansion culture of the mesenchymal stem cells, the mesenchymal stem cell can be cultured in the liquid medium in which a recombinant gelatin has been dissolved. According to a preferred aspect described above, the liquid medium in which a recombinant gelatin having an amino acid sequence derived from a partial amino acid sequence of collagen has been dissolved is a liquid medium for maintaining undifferentiation. According to a preferred aspect described above, it is possible to suppress differentiation of mesenchymal stem cells into adipocytes, with a simple operation (addition of recombinant gelatin to the differentiation induction medium is not needed) that the recombinant gelatin is added to the medium only at the time of the maintenance or expansion culture of the mesenchymal stem cells.

<Recombinant Gelatin>

The recombinant gelatin as used herein means a polypeptide or protein-like substance having an amino acid sequence similar to that of gelatin, which is produced by a gene recombination technology. It is preferable that the recombinant gelatin that can be used in the invention has repeats of a sequence represented by Gly-X-Y (where X and Y each independently represent any amino acid residue), which is characteristic to collagen. Here, a plurality of the Gly-X-Y sequences may be identical to or different from one another. Preferably, two or more sequences of cell adhesion signals are included in one molecule. Regarding the recombinant gelatin, a gelatin having an amino acid sequence derived from a partial amino acid sequence of human collagen can be used. For example, the gelatins described in EP1014176B, U.S. Pat. No. 6,992,172B, WO2004/085473A, and WO2008/103041A can be used; however, the examples are not limited to these. Preferred examples of the recombinant gelatin that is used in the invention are gelatins of the following embodiments.

A recombinant gelatin has the original properties of naturally occurring gelatin and thus has excellent biocompatibility. Also, since it is not a substance derived from a natural source, a recombinant gelatin has no risk of bovine spongiform encephalopathy (BSE) or the like, and has an excellent characteristic of being non-infectious. Since the recombinant gelatin does not include animal-derived components, it is possible to culture the mesenchymal stem cells under conditions of non-use of serum (Serum free) and non-use of the animal-derived components (Xeno free). Since a recombinant gelatin is homogeneous compared to naturally occurring gelatin and has a predetermined sequence, it is possible to precisely design a recombinant gelatin.

The molecular weight of the recombinant gelatin is not particularly limited; however, the molecular weight is preferably from 2,000 to 100,000 (from 2 kDa to 100 kDa), more preferably from 2,500 to 95,000 (from 2.5 kDa to 95 kDa), even more preferably from 5,000 to 90,000 (from 5 kDa to 90 kDa), and most preferably from 10,000 to 90,000 (from 10 kDa to 90 kDa).

It is preferable that the recombinant gelatin has repeats of a sequence represented by Gly-X-Y, which is characteristic to collagen. Here, a plurality of the Gly-X-Y sequences may be identical to or different from one another. In regard to the sequence Gly-X-Y, Gly represents glycine, and X and Y each independently represent any amino acid (preferably, any arbitrary amino acid other than glycine). The sequence represented by Gly-X-Y characteristic to collagen is a highly specific partial structure present in the amino acid compositions and sequences of gelatin and collagen, compared to other proteins. In this partial structure, glycine accounts for about one-third of the whole composition, and in the amino acid sequence, glycine repeatedly appears at a rate of one in every three amino acid residues. Glycine is the simplest amino acid, and there are fewer restrictions to the arrangement in a molecular chain. Thus, glycine greatly contributes to regeneration of the helix structure in the case of gelation. It is preferable that the amino acids represented by X and Y include a large proportion of imino acids (proline and oxyproline), and imino acids account for 10% to 45% of the total amount of the amino acids. Preferably, amino acids that account for 80% or more, even more preferably 95% or more, and most preferably 99% or more, of the sequence of the recombinant gelatin, constitute the repeating structure of Gly-X-Y.

In general gelatins, polar amino acids that have an electric charge and polar amino acids that are uncharged exist at a ratio of 1:1. Here, the term polar amino acid specifically refers to cysteine, aspartic acid, glutamic acid, histidine, lysine, asparagine, glutamine, serine, threonine, tyrosine, or arginine, and among these, polar uncharged amino acids include cysteine, asparagine, glutamine, serine, threonine, and tyrosine. In regard to the recombinant gelatin used in the invention, the proportion of polar amino acids among all the amino acids that constitute the recombinant gelatin is 10% to 40%, and preferably 20% to 30%. Meanwhile, the proportion of uncharged amino acids in the polar amino acids is 5% or more and less than 20%, and preferably 5% or more and less than 10%. It is also preferable that any one kind of amino acid, and preferably two or more kinds of amino acids, of serine, threonine, asparagine, tyrosine, and cysteine are not included in the amino acid sequence.

Generally, in regard to polypeptides, minimal amino acid sequences that function as cell adhesion signal sequences are known (for example, "Byotai Seiri (Pathophysiology)", Vol. 9, No. 7 (1990), p. 527, published by Nagai Shoten Co., Ltd.). It is preferable that the recombinant gelatin used in the invention contains two or more such cell adhesion signals in one molecule.

Regarding specific sequences, from the viewpoint of being applicable to many kinds of adhering cells, sequences of an RGD sequence, a LDV sequence, a REDV sequence (SEQ ID NO: 2), a YIGSR sequence (SEQ ID NO: 3), a PDSGR sequence (SEQ ID NO: 4), a RYVVLPR sequence (SEQ ID NO: 5), a LGTIPG sequence (SEQ ID NO: 6), a RNIAEIIKDI sequence (SEQ ID NO: 7), an IKVAV sequence (SEQ ID NO: 8), a LRE sequence, a DGEA sequence (SEQ ID NO: 9), and a HAV sequence, which are expressed in one-letter codes of amino acids, are preferred. Even more preferred sequences include an RGD sequence, a YIGSR sequence (SEQ ID NO: 3), a PDSGR sequence (SEQ ID NO: 4), a LGTIPG sequence (SEQ ID NO: 6), an IKVAV sequence (SEQ ID NO: 8), and a HAV sequence, and particularly preferred is an RGD sequence. Among RGD sequences, an ERGD sequence (SEQ ID NO: 10) is preferred. In a case in which a recombinant gelatin having cell adhesion signal sequences is used, the amount of cell matrix production can be increased. For example, in a case of chondrocyte differentiation in which mesenchymal stem cells are used as cells, the production of glycosaminoglycans (GAG) can be increased.

In regard to the disposition of RGD sequences in the recombinant gelatin used in the invention, it is preferable that the number of amino acids between RGD sequences is between 0 and 100, and preferably between 25 and 60, and is not uniform.

The content of these minimal amino acid sequences is preferably 3 to 50, even more preferably 4 to 30, particularly preferably 5 to 20, and most preferably 12, in one molecule of protein, from the viewpoints of cell adhesion and proliferation properties.

In regard to the recombinant gelatin used in the invention, the proportion of the RGD motifs with respect to the total number of amino acid residues is preferably at least 0.4%. In a case in which a gelatin includes 350 or more amino acid residues, it is preferable that each stretch of 350 amino acid residues includes at least one RGD motif. The proportion of the RGD motif with respect to the total number of amino acid residues is even more preferably at least 0.6%, still more preferably at least 0.8%, even still more preferably at least 1.0%, further still more preferably at least 1.2%, and most preferably at least 1.5%. The number of RGD motifs within a peptide is preferably at least 4, even more preferably at least 6, still more preferably at least 8, and further still more preferably from 12 to 16, per 250 amino acid residues. The proportion of 0.4% of the RGD motifs corresponds to at least one RGD sequence per 250 amino acid residues. Since the number of the RGD motifs is an integer, in order to satisfy the characteristic requirement of at least 0.4%, a gelatin molecule containing 251 amino acid residues must include at least two RGD sequences. Preferably, the gelatin of the invention includes at least two RGD sequences per 250 amino acid residues; more preferably includes at least three RGD sequences per 250 amino acid residues; and even more preferably includes at least four RGD sequences per 250 amino acid residues. According to another embodiment of the gelatin of the invention, the gelatin includes at least four RGD motifs, preferably at least six RGD motifs, more preferably at least eight RGD motifs, and even more preferably from 12 to 16 RGD motifs.

The recombinant gelatin may be partially hydrolyzed.

Preferably, an amino acid sequence of the recombinant gelatin used in the invention is represented by Formula: A-[(Gly-X-Y)n]$_m$-B. n units of X each independently represent any one amino acid residue, and n units of Y each independently represent any one amino acid residue. m preferably represents an integer from 2 to 10 and more preferably from 3 to 5. n preferably represents an integer from 3 to 100, even more preferably 15 to 70, and most preferably 50 to 65. A represents any amino acid residue or amino acid sequence, and B represents any amino acid residue or amino acid sequence. n units of Gly-X-Y may be identical to or different from one another.

More preferably, the amino acid sequence of the recombinant gelatin used in the invention is represented by Formula: Gly-Ala-Pro-[(Gly-X-Y)$_{63}$]$_3$-Gly (SEQ ID NO: 11) (in the formula, 63 units of X each independently represent any one amino acid residue; 63 units of Y each independently represent any one amino acid residue; and 63 units of Gly-X-Y may be identical to or different from one another).

It is preferable that a plurality of the sequence units of naturally occurring collagen are bonded to the repeating unit. The naturally occurring collagen as used herein may be any collagen substance that exists in nature; however, the collagen is preferably type I, type II, type III, type IV, or type V collagen. The collagen is more preferably type I, type II, or type III collagen. According to another embodiment, the source of the above-mentioned collagens is preferably human, cow, pig, mouse, or rat, and more preferably a human source.

The isoelectric point of the recombinant gelatin used in the invention is preferably 5 to 10, more preferably 6 to 10, and even more preferably 7 to 9.5. For the measurement of the isoelectric point of the recombinant gelatin, there is no limitation as long as it is a known method capable of measuring the isoelectric point. For example, the isoelectric point can be measured by measuring a pH of a 1 mass % gelatin solution after passing through a mixed crystal column of cation and anion exchange resin, according to an isoelectric focusing method (see Maxey, C. R. (1976); Phitogr. Gelatin 2, Editor Cox, P. J. Academic, London, Engl.).

Preferably, the recombinant gelatin is not deaminated.

Preferably, the recombinant gelatin does not have a telopeptide.

Preferably, the recombinant gelatin is a substantially pure polypeptide produced from a nucleic acid that encodes an amino acid sequence.

The recombinant gelatin used in the invention is particularly preferably:
(1) the amino acid sequence set forth in SEQ ID NO:1; or
(2) an amino acid sequence having cell adhesiveness and having at least 80% (even more preferably at least 90%, particularly preferably at least 95%, and most preferably at least 98%) sequence identity with the amino acid sequence set forth in SEQ ID NO:1.

The hydrophilicity value "1/IOB" value of the recombinant gelatin used in the invention is preferably from 0 to 1.0. The hydrophilicity value is more preferably from 0 to 0.6, and even more preferably from 0 to 0.4. IOB is an index of hydrophilicity/hydrophobicity based on an organic conceptual diagram showing the polarity/non-polarity of organic compounds suggested by FUJITA, Atsushi, and the details thereof are explained in, for example, "Pharmaceutical Bulletin", Vol. 2, 2, pp. 163-173 (1954), "Kagaku no Ryoiki (Domain of Chemistry)", Vol. 11, 10, pp. 719-725 (1957), and "Fragrance Journal", Vol. 50, pp. 79-82 (1981). To describe briefly, the root of all organic compounds is considered to be methane (CH4), and other compounds are all regarded as derivatives of methane. Certain values are set respectively for the number of carbon atoms, substituents, modified parts, rings, and the like of the compounds, and the scores are added to determine the organic values (OV) and the inorganic values (IV). These values are plotted on a graph, with the X-axis representing the organic values and the Y-axis representing the inorganic values. The IOB in the organic conceptual diagram means the ratio of the inorganic value (IV) with respect to the organic value (OV) in the organic conceptual diagram, that is, "inorganic value (IV)/organic value (OV)". Regarding the details of the organic conceptual diagram, reference can be made to "Shinpan Yuki Gainenzu—Kiso to Oyo—(New Edition Organic Conceptual Diagram—Fundamentals and Applications —)" (written by KODA, Yoshio, et al., Sankyo Shuppan Co., Ltd., 2008). In the present specification, hydrophilicity-and-hydrophobicity is indicated with the "1/IOB" value, which is the reciprocal of JOB. As the "1/IOB" value is smaller (closer to 0), this indicates that the compound is hydrophilic.

In the recombinant gelatin used in the invention, the hydrophilicity/hydrophobicity index represented by the Grand average of hydropathicity (GRAVY) value is preferably 0.3 or lower and −9.0 or higher, and even more preferably 0.0 or lower and −7.0 or higher. The Grand average of hydropathicity (GRAVY) value can be obtained by the method in "Gasteiger E., Hoogland C., Gattiker A., Duvaud S., Wilkins M. R., Appel RD., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

The recombinant gelatin used in the invention can be produced by a gene recombination technology that is known to those ordinarily skilled in the art, and the recombinant gelatin can be produced according to the methods described in, for example, EP1014176A2, U.S. Pat. No. 6,992,172B, WO2004/085473A, and WO2008/103041A. Specifically, a gene that encodes the amino acid sequence of a predetermined recombinant gelatin is obtained, this is incorporated into an expression vector to produce a recombinant expression vector, and this is introduced into an appropriate host. Thus, a transformant is produced. The transformant thus obtained is cultured in an appropriate medium, and thereby, a recombinant gelatin is produced. Then, the recombinant gelatin thus produced is collected from the culture product. Thereby, the recombinant gelatin used in the invention can be obtained.

In the invention, the recombinant gelatin is added to the liquid medium during mesenchymal stem cell culture. A content of the recombinant gelatin in the liquid medium in which the recombinant gelatin has been dissolved is not particularly limited as long as an effect of the invention can be achieved, but is generally 0.1 ng/mL to 500 μg/mL, and preferably 1 ng/mL to 300 μg/mL. The content of the recombinant gelatin in the liquid medium in the invention is significantly lower than a peptide content described in the prior art document (the amount is approximately 1/100,000 times). Thus, according to the invention, even with a smaller addition amount, it is possible to achieve an excellent effect (suppression of differentiation into adipocytes). In the invention, it is not needed to coat culture equipment with a recombinant gelatin.

The concentration of the recombinant gelatin in the liquid medium in which the recombinant gelatin has been dissolved is not particularly limited, but is preferably 0.01 μg/mL or more, more preferably 0.02 μm/mL or more, and even more preferably 0.01 μg/mL or more, and most preferably 1 μg/mL or more, in terms of performance of suppressing differentiation into adipocytes. The concentration of the recombinant gelatin is preferably less than 500 μg/mL, more preferably less than 300 μg/mL, even more preferably less than 50 μg/mL, and most preferably less than 10 μg/mL, in terms of a cell proliferation rate.

The concentration of the recombinant gelatin in the liquid medium in which the recombinant gelatin has been dissolved is preferably 0.01 μg/mL or more and less than 500 μg/mL, more preferably 0.02 μg/mL or more and less than 300 μg/mL, and even more preferably 1 μg/mL or more and less than 50 μg/mL, and most preferably 1 μg/mL or more and less than 10 μg/mL.

<Medium>

The type of liquid medium is not particularly limited as long as the type thereof is a medium that can maintain or expand culture the mesenchymal stem cells. For example, examples thereof can include MesenPro (containing 2% serum, Life Technologies), Dulbecco's modified Eagle medium (DMEM)/F12 (containing 20% fetal bovine serum (FBS) (Gibco), Life Technologies), DMEM (containing 10% FBS (Gibco), SIGMA), PRIME-XV XSFM (serum free, JX energy), MSCGM BulletKit (trademark) (Takara Bio), Mesencult-ACF (containing no animal-derived component) and Mesencult-SF (serum free, both Veritas), and MSCGM BullrtKit (containing serum, Lonza).

<Mesenchymal Stem Cell>

The mesenchymal stem cell (MSC) used in the invention is a cell having ability to replicate as an undifferentiated cell and having ability to differentiate into a bone cell, chondrocyte, cardiomyocyte, and adipocyte.

An origin of the mesenchymal stem cell is not particularly limited, and may be a human mesenchymal stem cell or a mesenchymal stem cell derived from a non-human animal such as a mouse, rat, cat, or dog.

It is known that the mesenchymal stem cell can be obtained from various tissue such as bone marrow, cartilage, adipose tissue, placental tissue, umbilical cord tissue, and dental pulp. An origin thereof is not particularly limited, but the mesenchymal stem cell is preferably a cell derived from bone marrow cells, a cell derived from cartilage, or a cell derived from fat.

The mesenchymal stem cell may be an autologous cell of a patient to which administration is performed or a heterologous cell.

As a method for isolating the mesenchymal stem cells from each tissue, a conventionally known method can be employed. For example, the mesenchymal stem cells can be suitably separated from tissue by a collagenase method. For example, the mesenchymal stem cells can be collected using a cell surface marker (such as CD105, CD73, or CD90) as an index.

<Culture>

As culture conditions for culturing the mesenchymal stem cells in the liquid medium in which the recombinant gelatin has been dissolved, general cell culture conditions may be selected. Examples thereof include conditions of 37° C. and 5% CO2. During culture, it is preferable to change the medium at an appropriate interval (preferably once every 1 to 7 days, more preferably once every 3 to 4 days). A culture period is not particularly limited, and the culture can be performed for 1 to 20 days, preferably 3 to 15 days, and more preferably 3 to 10 days.

For culture, a cell culture container such as a plate, a dish, a cell culture flask, and a cell culture bag can be used. As the cell culture bag, a gas permeable bag is suitable. In a case in which a large number of cells are required, a large culture tank may be used. Culture can be performed in either an open system or a closed system.

<Mesenchymal Stem Cell in which Differentiation into Adipocyte is Suppressed>

The mesenchymal stem cell, which is produced by the method of an embodiment of the invention and in which differentiation into an adipocyte is suppressed refers to a mesenchymal stem cell in which ability to differentiate into adipocytes is suppressed compared to a mesenchymal stem cell cultured in a liquid medium that does not contain the recombinant gelatin.

The ability to differentiate into adipocytes can be evaluated by confirming differentiation into adipocytes after performing differentiation induction into adipocytes by culturing mesenchymal stem cells in an adipocyte differentiation induction medium. Adipocytes can be detected by using, for example, morphological changes of cells, characteristic properties of adipocytes, or specific markers. Adipocytes accumulate fat in a cell. Accordingly, adipocytes can be detected by staining intracellular fat using Oil Red 0. In addition, examples of the specific markers of (brown) adipocytes include UCP1, Elongation of very long chain fatty acid protein 3 (EVOL3), PPAR gamma coactivatorl-alpha (PGC1A), PRD1-BF1-RIZ1 homologous domain containing 16 (PRDM16), and Cell Death-Inducing DFFA-Like Effector A (CIDEA), and adipocytes can be detected using these as indices. The UCP1 is a kind of uncoupling protein. For detection of the specific marker, a quarantine method (detection by an antibody) can be used. However, for a protein molecule, detection may be carried out by quantifying its mRNA amount thereof.

According to the invention, there is provided a mesenchymal stem cell produced by the production method of an embodiment of the invention. The mesenchymal stem cell produced by the method of an embodiment of the invention can be used for cell transplantation. Specifically, the cells of an embodiment of the invention can be used for the purpose of cell transplantation at a disease site. As a transplantation method, an incision or an endoscopy can be used.

<Method for Producing Differentiation-Induced Cell>

According to the invention, there is provided a method for producing a cell, including: a step of producing a mesenchymal stem cell in which differentiation into an adipocyte is suppressed by the method of the embodiment of the invention described above; and a step of culturing the mesenchymal stem cell in which differentiation into an adipocyte is suppressed in a medium for inducing differentiation. According to the method, a desired cell can be manufactured, as long as it is a cell which can be differentiation-induced from a mesenchymal stem cell. Examples of the cell that can be differentiation-induced from a mesenchymal stem cell can include, but are not limited to, a bone cell, chondrocyte, cardiomyocyte, and adipocyte.

The differentiation induction medium can be appropriately selected according to a type of a desired cell to be differentiation-induced.

In a case of performing differentiation induction into the bone cell, Lonza: Human Mesenchymal Stem Cell Osteogenic Differentiation Medium Bullet Kit or the like can be used.

In a case of performing differentiation induction into the chondrocyte, Lonza: Human Mesenchymal Stem Cell Chondrogenic Differentiation Medium Bullet Kit or the like can be used.

In a case of performing differentiation induction into the cardiomyocyte, for example, a method described in JP2009-136209A can be used.

In a case of performing differentiation induction into the adipocyte, Lonza: Human Mesenchymal Stem Cell Adipogenic Differentiation Medium BulletKit, Promo-Cell: Mesenchymal Stem Cell Adipogenic Differentiation Medium, or the like can be used.

Culture conditions for the differentiation induction (culture conditions other than the medium) are the same as the culture conditions for culturing the mesenchymal stem cells in the liquid medium in which the recombinant gelatin has been dissolved. A culture period for the differentiation induction is not particularly limited, but is generally 3 to 21 days and preferably 7 to 18 days.

According to the invention, there is further provided a differentiation-induced cell produced by the method for producing a cell described above. The cell of an embodiment of the invention described above can be used for cell transplantation. Specifically, the differentiation-induced cells of an embodiment of the invention can be used for the purpose of cell transplantation at a disease site. As a transplantation method, an incision or an endoscopy can be used.

<Inhibitor of Differentiation into Adipocyte>

According to the invention, there is provided an inhibitor of differentiation into an adipocyte, including: a recombinant gelatin having an amino acid sequence derived from a partial amino acid sequence of collagen. Details of the recombinant gelatin are as described in the present specification. The recombinant gelatin can be used as an inhibitor of differentiation into an adipocyte, by being dissolved in a liquid medium for culturing the mesenchymal stem cell, as described in the present specification. A form of the recombinant gelatin in a case of being provided as an inhibitor of differentiation into an adipocyte is not particularly limited. The recombinant gelatin may be provided as a solution or powder, or may also be provided in a state in which the recombinant gelatin is dissolved in a liquid medium.

The invention will be described more specifically using the following Examples, but the invention is not limited to the following Examples.

EXAMPLES

[Reference Example 1] Recombinant Gelatin

As a recombinant gelatin, the following CBE3 was prepared (described in WO2008/103041A).

CBE3: Molecular weight: 51.6 kD Structure: Gly-Ala-Pro[(Gly-XY)$_{63}$]$_3$-Gly (SEQ ID NO: 11) Number of amino acid residues: 571

RGD sequence: 12 sequences Imino acid content: 33% Almost 100% of the amino acid residues constitute a repeating structure of Gly-X-Y.

Serine, threonine, asparagine, tyrosine, and cysteine were not included in the amino acid sequence of CBE3.

CBE3 includes an ERGD sequence (SEQ ID NO: 10).

Isoelectric point: 9.34

GRAVY value: −0.682

I/IOB value: 0.323 Amino acid sequence (SEQ ID NO:1 in the Sequence Listing) (Identical to SEQ ID NO:3 disclosed in WO2008/103041A. However, X at the end was corrected to "P")

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)$_3$G

[Example 1] Adipogenic Differentiation Induction Experiment Using Cartilage-Derived Cell Yub2505 and Bone Marrow-Derived Cell UDE BM (1) Experiment 1: CBE3 added (addition amount: 28 ng/mL)
Experiment 2: No CBE3 added
(2) Material
Cells Used:
Yub2505 (cartilage-derived cells established at the National Center for Child Health and Development (hereinafter, NCCHD))
1Yub2505 was established according to a method described in Reference (Nasu M, Takayama S, Umezawa A. Endochondral ossification model system: designed cell fate of human epiphyseal chondrocytes during long-term implantation. J. Cell Physiol. 2015; 230: 1376-1388).
UDE BM (Bone marrow-derived cells established by NCCHD)
  UDE BM was established by the following method. Bone marrow fluid was extracted from the bone and cells were collected by density gradient centrifugation. The collected cells were washed with phosphate buffered saline (PBS), seeded in a DMEM (containing 10% FBS) medium, and cultured. Cells adhered to a culture container were collected.
Medium Used:
MesenPro (containing 2% serum, Life Technologies): Yub2505, UDE BM
DMEM/F12 (containing 20% FBS (Gibco), Life Technologies): Yub2505
DMEM (containing 10% FBS (Gibco), SIGMA): UDE BM
PRIME-XV XSFM (serum free, JX energy): Yub2505, UDE BM
Adipogenic differentiation induction medium: Human Mesenchymal Stem Cell Adipogenic Differentiation Medium BulletKit(Lonza)
0.1 mass % CBE3 aqueous solution: CELLNEST® (Fuji Film)
(3) Method
All of the following cell cultures were performed at 37° C. and 5% CO2.
Each cell was maintained and cultured by dispensing 8 mL of MesenPro medium in a culture dish having a diameter of 10 cm. The cell seeding amount was set to 1×10$^6$ cells/culture dish, and a culture period was set to 5 to 7 days.
The medium was replaced with MesenPro (8 mL). At that time, CBE3 was added to be 28 ng/mL. In Control, PBS (Nacalai Tesque) was added instead of the CBE3. A culture period was set to 7 days.
The CBE3 was added to each 2 mL medium (MesenPro, DMEM, and PRIME-XV XSFM) to be 28 ng/mL and used (in Control, PBS (Nacalai Tesque) was added instead of the CBE3 and used), subculture was performed to a 6-well plate and pre-culture was performed. The cell seeding amount was set to 0.2×10$^6$ cells/well, and a culture period was set to 3 days.
The medium was replaced with an adipogenic differentiation induction medium (2 mL), and differentiation induction was started. In this case, differentiation was induced every 3 or 4 days, and the medium and the maintenance medium were alternately replaced with each other. A differentiation induction period was set to 2 weeks.
The medium was replaced with a maintenance medium (2 mL), and maintenance culture was performed. A maintenance culture period was set to 7 days.
The cells were stained with oil red and 25 screens were photographed with a microscope. Accordingly, differentiation into adipocytes was confirmed.
(4) Results
Results of confirming differentiation into adipocytes are shown in FIGS. 1 to 4.
In any combination of a case in which the cells are UDE BM and the medium is MesenPro (FIG. 1), a case in which the cells are UDE BM and the medium is DMEM (FIG. 2), a case in which the cells are UDE BM and the medium is PRIME-XV (FIG. 3), and a case in which the cells are Yub2505 and the medium is PRIME-XV (FIG. 4), in Experiment 1 (CBE3 added), differentiation into adipocytes was suppressed, compared to Experiment 2 (no CBE3 added).

[Example 2] Adipogenic Differentiation Induction Experiment Using Human Bone Marrow-Derived Cells BMSC (1) Experiment: CBE3 added (addition amount: 0, 0.028, 2.8, 28, and 280 µg/mL)
(2) Material
Cells Used:
Human bone marrow-derived cells BMSC (Lonza: PT-2501)
Medium Used:
MesenPro (containing 2% serum, Life Technologies)
Adipogenic differentiation induction medium: Human Mesenchymal Stem Cell Adipogenic Differentiation Medium BulletKit (Lonza), PromoCell:Mesenchymal Stem Cell Adipogenic Differentiation Medium
0.1 mass % CBE3 aqueous solution: CELLNEST® (Fuji Film)
(3) Method
All of the following cell cultures were performed at 37° C. and 5% CO2.
BMSC cells were maintained and cultured by dispensing 8 mL of MesenPro medium in a culture dish having a diameter of 10 cm. The cell seeding amount was set to 5×10$^5$ cells/well, and a culture period was set to 6 days.
The CBE3 was added to 2 mL MesenPro medium to be 0 to 280 µg/mL and used (in Control, PBS (Nacalai Tesque) was added instead of the CBE3 and used), subculture was performed to a 6-well plate (Falcon TC), and pre-culture was performed. The cell seeding amount was set to 1.5×10$^5$ cells/well, and a culture period was set to 4 days.
The medium was replaced with a 2 mL adipogenic differentiation induction medium (Lonza/PromoCell), and differentiation induction was started. In the Lonza medium, differentiation was induced every 3 or 4 days, and the medium and the maintenance medium were alternately replaced with each other. In the PromoCell medium, the differentiation induction medium was changed every 3 or 4 days. A differentiation induction period was set to 17 days.

The medium was replaced with a maintenance medium (2 mL), and maintenance culture was performed. A maintenance culture period was set to 1 day.

The cells were stained with oil red and 25 screens were photographed with a microscope (KEYENCE BZ-X700). Accordingly, differentiation into adipocytes was confirmed. Detection objects of 300 μm² or smaller were not counted as adipocytes, and those larger than 300 μm² were counted.

(4) Results

Figure 6A:
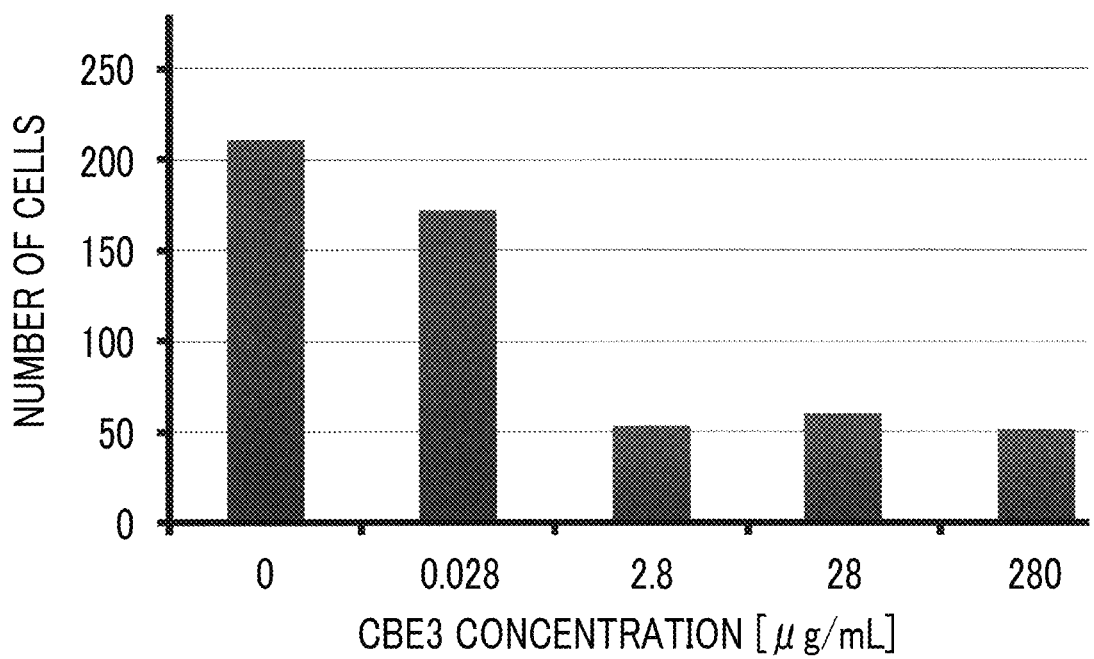
FIGS. 6A and 6B show results of counting the number of cells differentiated into adipocytes, in micrographs of FIGS. 5A and 5B.
Figure 6B:
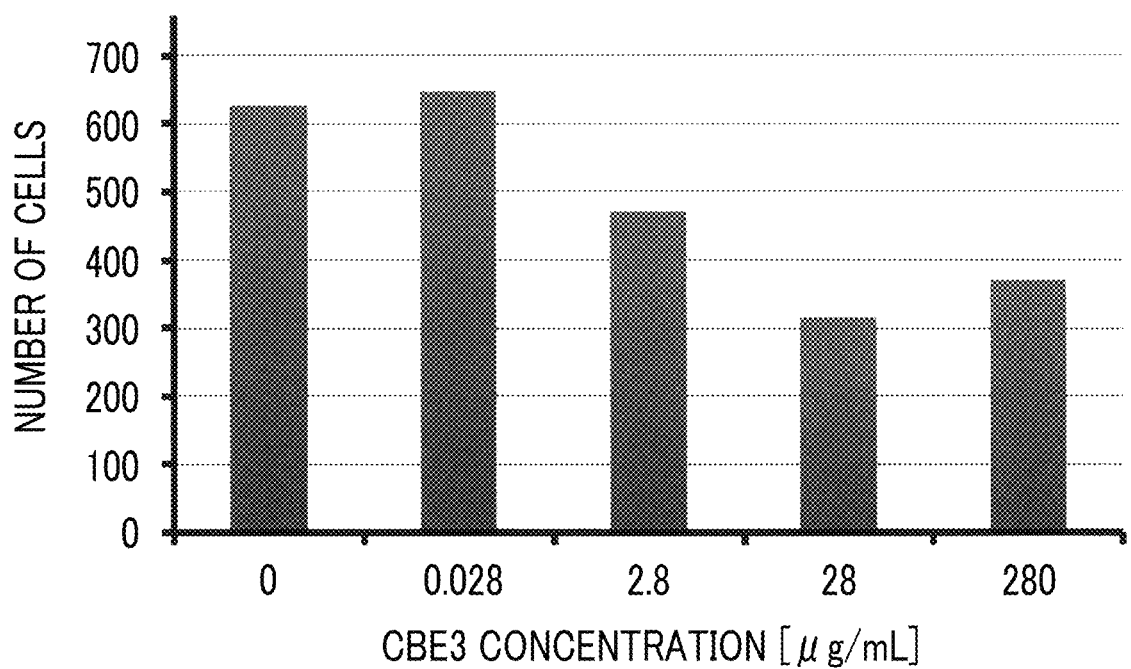

Results of confirming differentiation into adipocytes are shown in FIGS. 5A to 6B. (FIGS. 6A and 6B shows results of counting the number of cells differentiated into adipocytes using adipocyte-staining photographs in FIGS. 5A and 5B)

Even in a case in which the cells were BMSC and the medium was MesenPro or a case in which the adipogenic differentiation induction medium was any of Lonza or PromoCell, the adipogenic differentiation was suppressed by adding CBE3. In a case in which the addition amount of CBE3 was from 2.8 to 280 μg/mL, adipogenic differentiation was significantly suppressed.

[Example 3] Adipogenic Proliferation Experiment Using Human Bone Marrow-Derived Cells BMSC (1) Experiment: CBE3 added (addition amount: 0, 0.028, 2.8, and 28 μg/mL)

(2) Material

Cells used:

Human bone marrow-derived cells BMSC (Lonza: PT-2501)

Medium used: MesenPro (containing 2% serum, Life Technologies)

0.1 mass % CBE3 aqueous solution: CELLNEST® (Fuji Film)

(3) Method

All of the following cell cultures were performed at 37° C. and 5% CO2.

Cells were maintained and cultured until passage 5 (fifth passage cell) by dispensing 8 mL MesenPro medium in a culture dish having a diameter of 10 cm. The cell seeding amount was set to 0.4 to $1.0 \times 10^6$ cells/culture dish, and a culture period was set to 7 days for each passage.

The CBE3 was added to 2 mL MesenPro medium to be 0 to 28 μg/mL and used (in Control, PBS (Nacalai Tesque) was added instead of the CBE3 and used), subculture was performed to Passage 6 (sixth passage cell) to 10 cm culture dish (manufactured by Sumitomo Bakelite). The cell seeding amount was set to $0.4 \times 10^6$ cells/culture dish, and a culture period was set to 7 days. After 7 days, the number of cells was counted using Vi-Cell (BECKMAN COULTER).

(4) Results

Figure 7:
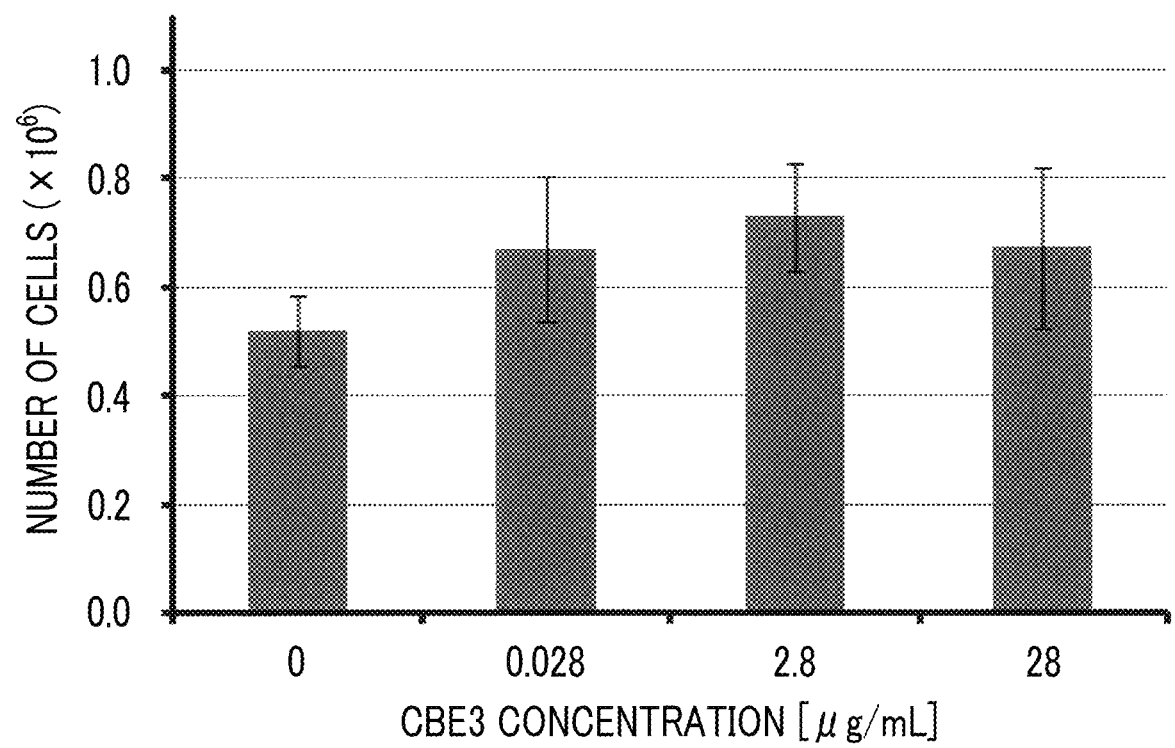
FIG. 7 shows results of measuring the number of cells by culturing cells with varying an addition amount of a recombinant gelatin, in a case in which the cells are BMSC (Lonza: PT-2501) and a medium is MesenPro.

FIG. 7 shows results of counting the number of cells. At each CBE3 concentration, culture was performed with N=3, and an average value of measurement results is shown. Compared to a case of no CBE3 added, the number of cells after 7 days of culture increased by adding CBE3. The increase in the number of cells peaked at 2.8 μg/mL, and the number of cells showed a decreasing trend at higher concentrations.

SEQUENCE LIST

International Application 18F00683 Method for Producing Mesenchymal Stem Cell JP18018391 20180511----00070437451800986822 Normal 20180511164909201804121441427380P1AP101_18_0.app Based on International Reception Patent Cooperation Treaty

---

What is claimed is:

1. A method for producing a mesenchymal stem cell, comprising:
   a step of culturing a mesenchymal stem cell in a liquid medium in which a recombinant gelatin having an amino acid sequence derived from a partial amino acid sequence of human collagen has been dissolved,
   wherein differentiation into an adipocyte is suppressed;
   wherein a molecular weight of the recombinant gelatin is 2,000 to 100,000 Da;
   wherein the amino acid sequence of the recombinant gelatin is represented by the following formula as SEQ ID NO: 11, Gly-Ala-Pro-[(Gly-X-Y)$_{63}$]$_3$-Gly in the formula, 63 units of X each independently represent any one amino acid residue; 63 units of Y each independently represent any one amino acid residue; and 63 units of Gly-X-Y may be identical to or different from one another;
   wherein the number of RGD sequences is 12 to 16; and
   wherein the amino acid sequence does not contain any two or more amino acids of serine, threonine, asparagine, tyrosine and cysteine.

2. The method according to claim 1,
   wherein the recombinant gelatin has repeats of a sequence represented by Gly-X-Y, which is characteristic to collagen,
   X and Y each independently represent any one amino acid residue,
   a plurality of the Gly-X-Y sequences may be identical to or different from one another, and
   a molecular weight of the recombinant gelatin is from 10 kDa to 90 kDa.

3. The method according to claim 1,
   wherein the recombinant gelatin includes
   (1) an amino acid sequence set forth in SEQ ID NO:1, or
   (2) an amino acid sequence having cell adhesiveness and having at least 90% sequence identity with the amino acid sequence set forth in SEQ ID NO:1.

4. The method according to claim 1,
   wherein the mesenchymal stem cell is a bone marrow-derived cell or a cartilage-derived cell.

5. The method according to claim 1,
   wherein the liquid medium in which a recombinant gelatin having an amino acid sequence derived from a partial amino acid sequence of collagen has been dissolved is a liquid medium for maintaining undifferentiation.

6. The method according to claim 1,
   wherein a concentration of the recombinant gelatin having an amino acid sequence derived from a partial amino acid sequence of collagen in the liquid medium in which the recombinant gelatin has been dissolved is from 0.01 µg/mL to 500 µg/mL.

7. The method according to claim 1,
   wherein a concentration of the recombinant gelatin having an amino acid sequence derived from a partial amino acid sequence of collagen in the liquid medium in which the recombinant gelatin has been dissolved is from 0.02 µg/mL to 300 µg/mL.

8. A method for producing a differentiation-induced cell, comprising:
   a step of producing a mesenchymal stem cell in which differentiation into an adipocyte is suppressed by the method according to claim 1; and
   a step of culturing the mesenchymal stem cell in which differentiation into an adipocyte is suppressed in a medium for inducing differentiation.

9. A method for producing a differentiation-induced cell, comprising:
   a step of producing a mesenchymal stem cell in which differentiation into an adipocyte is suppressed by the method according to claim 1; and
   a step of culturing the mesenchymal stem cell in which differentiation into an adipocyte is suppressed in a medium for inducing differentiation.

10. A method for producing a differentiation-induced cell, comprising:
    a step of producing a mesenchymal stem cell in which differentiation into an adipocyte is suppressed by the method according to claim 2; and
    a step of culturing the mesenchymal stem cell in which differentiation into an adipocyte is suppressed in a medium for inducing differentiation.

* * * * *

UNITED STATES PATENT AND TRADEMARK OFFICE
CERTIFICATE OF CORRECTION

| | |
|---|---|
| PATENT NO. | : 11,649,274 B2 |
| APPLICATION NO. | : 16/678873 |
| DATED | : May 16, 2023 |
| INVENTOR(S) | : Koji Muraya |

It is certified that error appears in the above-identified patent and that said Letters Patent is hereby corrected as shown below:

On the Title Page

Please change:
"(73) Assignee: FUJTFITM CORPORATION, Tokyo (JP)"
To:
-- (73) Assignee: FUJIFILM CORPORATION, Tokyo (JP) --

Signed and Sealed this
Fifteenth Day of August, 2023

Katherine Kelly Vidal
*Director of the United States Patent and Trademark Office*

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
```

```
            115                 120                 125
Arg Gly Leu Ala Gly Pro Ile Gly Pro Pro Gly Ala Gly Pro
    130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Pro
                180                 185                 190
Gly Ala Pro Gly Leu Gln Gly Ala Pro Gly Leu Gln Gly Met Pro Gly
                195                 200                 205
Glu Arg Gly Ala Ala Gly Leu Pro Gly Pro Lys Gly Glu Arg Gly Asp
    210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
                260                 265                 270
Asp Gly Val Arg Gly Leu Ala Gly Pro Ile Gly Pro Pro Gly Glu Arg
                275                 280                 285
Gly Ala Ala Gly Leu Pro Gly Pro Lys Gly Glu Arg Gly Asp Ala Gly
    290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
                340                 345                 350
Pro Lys Gly Glu Arg Gly Asp Ala Gly Pro Lys Gly Ala Asp Gly Ala
                355                 360                 365
Pro Gly Lys Asp Gly Val Arg Gly Leu Ala Gly Pro Pro Gly Ala Pro
                370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
                420                 425                 430
Gly Glu Arg Gly Ala Ala Gly Leu Pro Gly Pro Lys Gly Glu Arg Gly
                435                 440                 445
Asp Ala Gly Pro Lys Gly Ala Asp Gly Ala Pro Gly Lys Asp Gly Val
    450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
                500                 505                 510
Ile Gly Pro Pro Gly Pro Ala Gly Ala Pro Gly Ala Pro Gly Leu Gln
                515                 520                 525
Gly Met Pro Gly Glu Arg Gly Ala Ala Gly Leu Pro Gly Pro Lys Gly
                530                 535                 540
```

-continued

```
Glu Arg Gly Asp Ala Gly Pro Lys Gly Ala Asp Ala Pro Gly Lys
545                 550                 555                 560

Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic: adhesive sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Synthetic: adhesive sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic: adhesive sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: adhesive sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic: adhesive sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic: adhesive sequence
```

-continued

```
<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic: adhesive sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic: adhesive sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Synthetic: adhesive sequence

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(570)
<223> OTHER INFORMATION: Every Xaa can be any naturally occurring amino
      acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
                20                  25                  30

Xaa Gly Xaa Xaa Gly Xaa Xaa Gly Xaa Xaa Gly Xaa Xaa Gly Xaa Xaa
            35                  40                  45

Gly Xaa Xaa Gly Xaa Xaa Gly Xaa Xaa Gly Xaa Xaa Gly Xaa Xaa Gly
        50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95

Gly Xaa Xaa Gly Xaa Xaa Gly Xaa Xaa Gly Xaa Xaa Gly Xaa Xaa Gly
```

-continued

```
                100             105             110
Xaa Xaa Gly Xaa Xaa Gly Xaa Xaa Gly Xaa Xaa Gly Xaa Xaa Gly Xaa
        115             120             125
Xaa Gly Xaa Xaa Gly Xaa Xaa Gly Xaa Xaa Gly Xaa Xaa Gly Xaa Xaa
        130             135             140
Gly Xaa Xaa Gly Xaa Xaa Gly Xaa Xaa Gly Xaa Xaa Gly Xaa Xaa Gly
145             150             155             160
Xaa Xaa Gly Xaa Xaa Gly Xaa Xaa Gly Xaa Xaa Gly Xaa Xaa Gly Xaa
        165             170             175
Xaa Gly Xaa Xaa Gly Xaa Xaa Gly Xaa Xaa Gly Xaa Xaa Gly Xaa Xaa
        180             185             190
Gly Xaa Xaa Gly Xaa Xaa Gly Xaa Xaa Gly Xaa Xaa Gly Xaa Xaa Gly
        195             200             205
Xaa Xaa Gly Xaa Xaa Gly Xaa Xaa Gly Xaa Xaa Gly Xaa Xaa Gly Xaa
        210             215             220
Xaa Gly Xaa Xaa Gly Xaa Xaa Gly Xaa Xaa Gly Xaa Xaa Gly Xaa Xaa
225             230             235             240
Gly Xaa Xaa Gly Xaa Xaa Gly Xaa Xaa Gly Xaa Xaa Gly Xaa Xaa Gly
            245             250             255
Xaa Xaa Gly Xaa Xaa Gly Xaa Xaa Gly Xaa Xaa Gly Xaa Xaa Gly Xaa
        260             265             270
Xaa Gly Xaa Xaa Gly Xaa Xaa Gly Xaa Xaa Gly Xaa Xaa Gly Xaa Xaa
        275             280             285
Gly Xaa Xaa Gly Xaa Xaa Gly Xaa Xaa Gly Xaa Xaa Gly Xaa Xaa Gly
        290             295             300
Xaa Xaa Gly Xaa Xaa Gly Xaa Xaa Gly Xaa Xaa Gly Xaa Xaa Gly Xaa
305             310             315             320
Xaa Gly Xaa Xaa Gly Xaa Xaa Gly Xaa Xaa Gly Xaa Xaa Gly Xaa Xaa
        325             330             335
Gly Xaa Xaa Gly Xaa Xaa Gly Xaa Xaa Gly Xaa Xaa Gly Xaa Xaa Gly
        340             345             350
Xaa Xaa Gly Xaa Xaa Gly Xaa Xaa Gly Xaa Xaa Gly Xaa Xaa Gly Xaa
        355             360             365
Xaa Gly Xaa Xaa Gly Xaa Xaa Gly Xaa Xaa Gly Xaa Xaa Gly Xaa Xaa
        370             375             380
Gly Xaa Xaa Gly Xaa Xaa Gly Xaa Xaa Gly Xaa Xaa Gly Xaa Xaa Gly
385             390             395             400
Xaa Xaa Gly Xaa Xaa Gly Xaa Xaa Gly Xaa Xaa Gly Xaa Xaa Gly Xaa
        405             410             415
Xaa Gly Xaa Xaa Gly Xaa Xaa Gly Xaa Xaa Gly Xaa Xaa Gly Xaa Xaa
        420             425             430
Gly Xaa Xaa Gly Xaa Xaa Gly Xaa Xaa Gly Xaa Xaa Gly Xaa Xaa Gly
        435             440             445
Xaa Xaa Gly Xaa Xaa Gly Xaa Xaa Gly Xaa Xaa Gly Xaa Xaa Gly Xaa
        450             455             460
Xaa Gly Xaa Xaa Gly Xaa Xaa Gly Xaa Xaa Gly Xaa Xaa Gly Xaa Xaa
465             470             475             480
Gly Xaa Xaa Gly Xaa Xaa Gly Xaa Xaa Gly Xaa Xaa Gly Xaa Xaa Gly
            485             490             495
Xaa Xaa Gly Xaa Xaa Gly Xaa Xaa Gly Xaa Xaa Gly Xaa Xaa Gly Xaa
        500             505             510
Xaa Gly Xaa Xaa Gly Xaa Xaa Gly Xaa Xaa Gly Xaa Xaa Gly Xaa Xaa
        515             520             525
```

```
Gly Xaa Xaa Gly Xaa Xaa Gly Xaa Xaa Gly Xaa Xaa Gly Xaa Xaa Gly
    530             535             540

Xaa Xaa Gly Xaa Xaa Gly Xaa Xaa Gly Xaa Xaa Gly Xaa Xaa Gly Xaa
545             550             555             560

Xaa Gly Xaa Xaa Gly Xaa Xaa Gly Xaa Xaa Gly
        565             570
```